United States Patent [19]

Taylor

[11] Patent Number: 4,476,227
[45] Date of Patent: Oct. 9, 1984

[54] COSMID CLONING VECTORS

[75] Inventor: Dean P. Taylor, King of Prussia, Pa.

[73] Assignee: Smithkline Beckman Corporation, Philadelphia, Pa.

[21] Appl. No.: 433,062

[22] Filed: Oct. 6, 1982

[51] Int. Cl.$^3$ .................. C12N 1/00; C12N 15/00; C12N 1/20; C12P 21/00; C12P 19/34

[52] U.S. Cl. .................. 435/317; 435/172.3; 435/68; 435/91; 435/253

[58] Field of Search .................. 435/68, 70, 91, 172, 435/253, 317, 172.3

[56] References Cited

U.S. PATENT DOCUMENTS 4,304,863 12/1981 Collins .

FOREIGN PATENT DOCUMENTS 2462476 3/1981 France .

OTHER PUBLICATIONS

Hohn, Methods in Enzymology 68:299-309 (1979).
Collins, Methods in Enzymology 68:309-326 (1979).
Collins and Hohn, Proc. Natl. Acad. Sci. U.S.A. 75(9):4242-4246 (1978).
Meyerowitz et al., Gene 11:271-282 (1980).
Hohn and Collins, Gene 11:291-298 (1980).
Plasmid 8:100 (1982).
Taylor et al., J. Bacteriol. 137(1):92-104 (1979).
Hashimoto-Gotoh et al., Gene 16:227-235 (1981).
Baldacci et al., Nucl. Acids. Res. 9:3575-3588 (1981).
Marcoli et al., FEBS Letters 110(1):11-14 (1980).
Alton et al., Nature 282:864-869 (1979).
Nichols et al., J. Virol. 26(2):429-434 (1978).
Sutcliffe, Cold Spring Harbor Symposium 43:77-90 (1979).

Primary Examiner—Thomas Wiseman
Assistant Examiner—James Martinell
Attorney, Agent, or Firm—Edward T. Lentz; Janice E. Williams; Alan D. Lourie

[57] ABSTRACT

Small cosmid cloning vectors having two antibiotic resistance markers, selected from chloramphemicol resistance, streptomycin and spectinomycin resistance and tetracycline resistance markers, at least one having a unique restriction site.

6 Claims, 7 Drawing Figures

COSMID CLONING VECTORS

FIELD OF THE INVENTION

This invention relates to cosmid cloning vectors and their use in cloning large fragments of foreign DNA in bacteria.

BACKGROUND OF THE INVENTION

A cosmid cloning vector is a plasmid which contains a lambda or lambdoid phage cos site, that is, the recognition site essential for packaging of linear concatenated DNA into lambda or lambdoid phage heads; a replicon, at least one selectable genetic marker; and at least one unique restriction endonuclease site in a nonessential region. These DNA sequences are herein referred to as "cosmid DNA".

Cosmid cloning vectors can be used to clone foreign DNA by inserting the foreign DNA into a restriction site in the cosmid DNA, packaging the recombinant DNA in infectious phage particles, preferably in vitro, and transfecting $E.\ coli$ host cells. Once introduced into the host cells, the cosmids replicate in the manner of plasmids, due to the presence of the replicon. Transfected cells are selected based on a phenotypic trait contributed by the genetic marker, usually an antibiotic resistance marker.

Packaging is most efficient when the linear DNA to be packaged inside the phage head is about 23 to 31 Megadaltons (Md), that is, about 38 to 52 kilobase pairs (kb). Cosmid DNA can be considerably smaller than 52 kb. Thus, cosmid cloning vectors can be suitable for cloning large DNA fragments such as eukaryotic genes, which are typically interspersed in large sequences, and gene banks or libraries.

Hohn, *Methods in Enzymology* 68:299–309 (1979), and Collins, *Methods in Enzymology* 68:309–326 (1979), describe the morphogenesis of lambda phage particles and in vitro packaging of cosmid vectors. Several known cosmid vectors are described.

Collins and Hohn, *Proc. Natl. Acad. Sci. U.S.A.* 75(9):4242–4246 (1978), and Collins and Hohn, U.S. Pat. No. 4,304,863, disclose preparation of cosmids pJC703 and pJC720, 17.3 Md and 16 Md, respectively, each having a rifampicin resistance ($Rif^R$) marker, and a cosmid of about 27.5 Md having $Rif^R$ and ampicillin resistance ($Ap^R$) markers. The authors also disclose methods for in vitro packaging and transfection using cosmid cloning vectors containing foreign DNA.

Meyerowitz et al., *Gene* 11:271–282 (1980), describe construction of cosmids MUA-3, MUA-5 and MUA-10 and of eukaryotic gene libraries using MUA-3. The cosmids are about 3 Md and have tetracycline resistance ($Tc^R$) markers.

Hohn and Collins, *Gene* 11:291–298 (1980), describe construction of cosmid pHC79, about 6.4 kb, having the two markers of plasmid pBR322, $Ap^R$ and $Tc^R$.

At the Fifth Annual Mid-Atlantic Regional Conference on Extrachromosomal Genetic Elements, Oct. 9–11, 1981, Ocean City, Md., U.S.A., Taylor, the inventor of the cosmid cloning vector disclosed and claimed herein, reported cosmids pDPT5Cm and pDPT5Sp, each having two genetic markers: chloramphenicol resistance ($Cm^R$) and $Tc^R$ in the case of pDPT5Cm, and streptomycin and spectinomycin resistance ($Sm^R/Sp^R$) and $Tc^R$ in the case of pDPT5Sp. An abstract of this presentation is published at Plasmid 8:100 (1982).

Hashimoto-Gotoh et al., *Gene* 16:227–235 (1981), describe construction of cosmid pHSG422, about 8.8 kb, having $Ap^R$, $Cm^R$ and kanamycin resistance ($Km^R$) markers.

Baldacci et al., *Nucl. Acids. Res.* 9:3575–3588 (1981), describe cosmids pFF1 and pFF2, having a $Km^R$ marker. The cosmid, pFF1, is claimed in French Patent No. 2,462,476 (Derwent Accession Number 33928D).

As stated previously, there is an upper limit of about 52 kb on the size of cosmid cloning vectors which can be packaged efficiently. Therefore, in order to clone large foreign DNA fragments, it is desirable to have cosmid cloning vectors in which the cosmid DNA, that is, the DNA carrying the cos site, a replicon, a marker and a unique restriction site, is small. Further, to facilitate selection of transfected cells containing the desired cosmid vector and for subsequent subcloning, it is desirable to have cosmid vectors containing two genetic markers with at least one of the markers having a unique restriction site such that insertion of foreign DNA into that site detectably affects the phenotype of transfected cells by insertional inactivation of the marker.

SUMMARY OF THE INVENTION

The invention provides a cosmid cloning vector wherein the cosmid DNA, in addition to a cos site and a replicon, contains two selectable genetic markers selected from the group consisting of $Cm^R$, $Tc^R$ and $Sm^R/Sp^R$. Particular embodiments of the invention include the vector wherein the cosmid DNA is no more than about 7.5 kb, the markers are $Cm^R$ and $Tc^R$ or $Sm^R/Sp^R$ and $Tc^R$ and at least one of the markers has a unique restriction site for insertional inactivation. The invention also includes a plasmid cloning vector having $Sm^R/Sp^R$ and $Tc^R$ markers. The invention includes equivalents of the vectors claimed herein, such as, for example, RNA and single strand DNA.

BRIEF DESCRIPTION OF THE DRAWINGS

Following is a brief description of the drawings which are not drawn to scale but are illustrative of the invention or materials which may be used in practicing the invention.

DETAILED DESCRIPTION OF THE INVENTION

In the cosmid cloning vector of the invention, the cosmid DNA contains two selectable genetic markers selected from the group consisting of $Cm^R$, $Sm^R/Sp^R$ and $Tc^R$. The vector of the invention includes vectors substantially containing only cosmid DNA as well as recombinant molecules comprising cosmid DNA and foreign DNA. By "foreign DNA" is meant DNA other than cosmid DNA. Foreign DNA can be of eukaryotic or prokaryotic origin and might include, for example, one or more genes for expression and production of commercially useful products; one or more replicons recognized by other species, making the cosmid useful as a shuttle vector; and a deoxynucleotide sequence comprising all or part of an organism's genome, for banking or experimentation. The invention includes all forms of the vector, such as, for example, linear, concatameric and circular.

Figure 6:
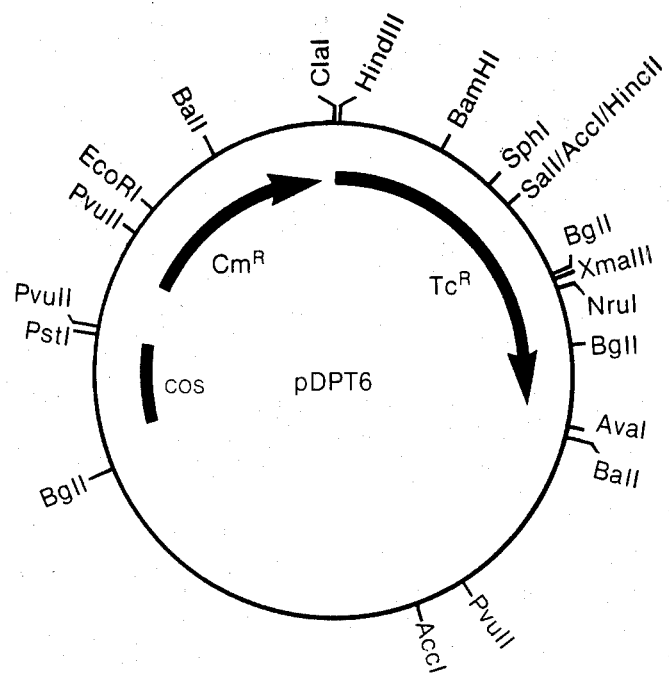
FIG. 6 is a restriction endonuclease cleavage map of pDPT6.

The preferred embodiment of the invention is about 5.4 kb and has a $Cm^R$ marker and a $Tc^R$ marker. Such cosmid is exemplified by pDPT6, characterized substantially as shown in FIG. 6. The cosmid DNA of pDPT6 has substantially the following unique sites: EcoRI in the $Cm^R$ gene; HindIII, BamHI, SphI, SalI, HincII, XmaIII and NruI in the $Tc^R$ gene; and ClaI, AvaI and PstI. All of the unique sites are suitable for cloning. The cosmid DNA lacks restriction sites for substantially the following restriction endonucleases: KpnI, BglII, HpaI, XhoI, StuI, SmaI, BstEII, SacII and PvuI. The replicon is derived from pBR322 and is positioned between the downstream end of the $Tc^R$ gene and the cos site.

In this context, by "substantially" is meant that the relative positions of the restriction sites and cosmid DNA sequences as illustrated and described are substantially accurate, that one or more restriction sites can be lost or gained by mutations not otherwise affecting the vector, and that additional sites for endonucleases which were not used in mapping procedures probably exist.

In pDPT6, the $Tc^R$ and $Cm^R$ genes are promoted independently, that is, each has its own promoter; transcription or inactivation of one marker does not affect the other. The $Tc^R$ promoter can be inactivated by insertion into the HindIII site immediately upstream of the $Tc^R$ structural gene. Both markers are transcribed in the same direction.

Figure 7:
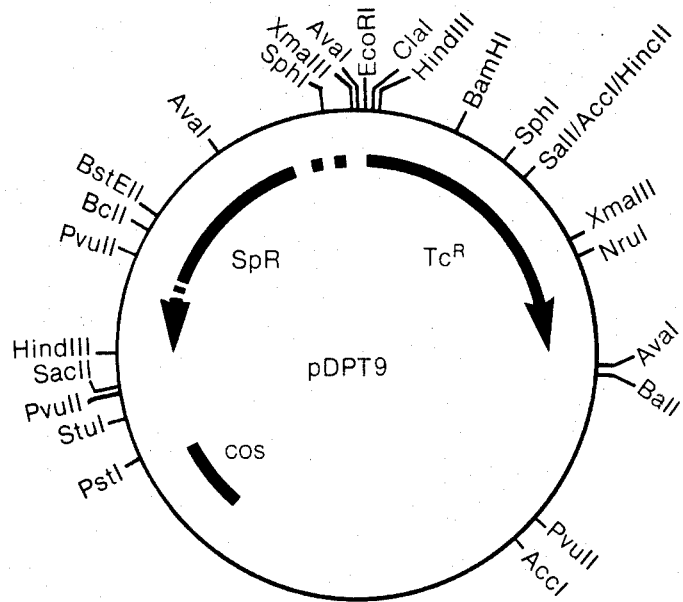
FIG. 7 is a restriction endonuclease cleavage map of pDPT9.

A second embodiment of the invention is exemplified by pDPT9, which is characterized substantially as shown in FIG. 7. It is about 6.3 kb and has a $Sm^R/Sp^R$ marker and a $Tc^R$ marker. The cosmid DNA has substantially the following unique restriction sites: BstEII and BclI in the $Sm^R/Sp^R$ gene; BamHI, SalI, HincII and NruI, in the $Tc^R$ gene; and EcoRI, ClaI, BalI, PvuII, PstI, StuI and SacII. All of the unique sites are suitable for cloning, although cloning in sites in the replicon region, such as the PvuII site, may adversely affect the replicon. The cosmid DNA lacks restriction sites for substantially the following restriction endonucleases: KpnI, XhoI, BglII and HpaI. The replicon, which is positioned between the downstream end of the $Tc^R$ gene and the cos site, is derived from pBR322. In pDPT9, the markers are promoted independently, but in opposite directions.

A third embodiment of the invention is exemplified by pDPT8. This cosmid is similar to pDPT9, differing in the orientation of the HindIII sequence carrying the $Sm^R/Sp^R$ structural gene and promoter and the $Tc^R$ promoter. It is believed that both markers are transcribed in the same direction from the $Sm^R/Sp^R$ promoter and that insertional inactivation of the $Sm^R/Sp^R$ marker will, therefore, also inactivate the $Tc^R$ gene.

Figure 4:
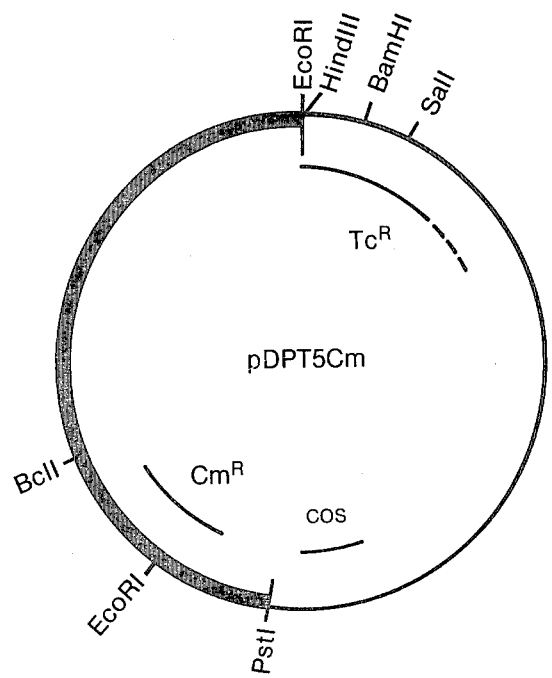
FIG. 4 is a restriction endonuclease cleavage map of pDPT5Cm.
Figure 5:
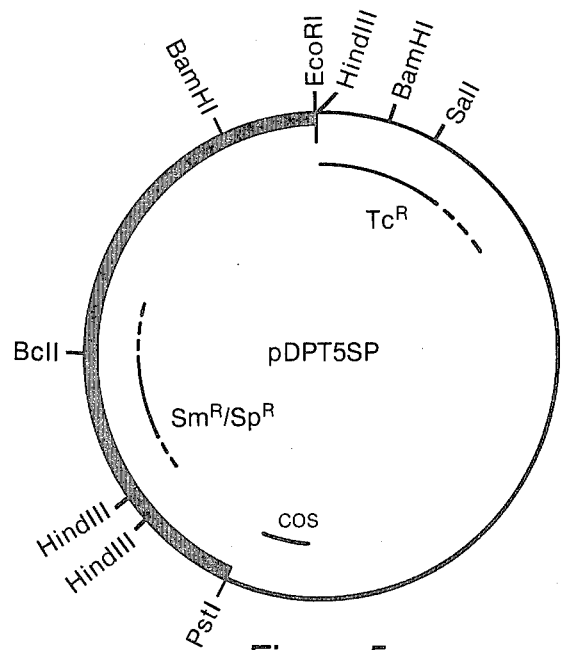
FIG. 5 is a restriction endonuclease cleavage map of pDPT5Sp.

Other cosmid vectors of the invention are exemplified by pDPT5Cm and pDPT5Sp which are characterized substantially as shown in FIGS. 4 and 5, respectively. pDPT5Cm is about 7.4 kb and has $Tc^R$ and $Cm^R$ markers, the former having unique HindIII, BamHI, SphI and SalI sites. Additionally, pDPT5Cm has unique sites for PstI and BclI. pDPT5Sp is 7.1 kb and has $Tc^R$ and $Sm^R/Sp^R$ markers, the former having unique SphI and SalI sites and the latter having unique BclI and BstEII sites. Other unique sites in pDPT5Sp are for EcoRI and PstI. The replicons in both vectors are derived from pBR322 and lie between the $Tc^R$ markers and the cos sites as in pDPT6 and pDPT9.

The cosmid cloning vectors of the invention can be prepared by ligating DNA fragments containing the lambda cos site, an E. coli replicon and two antibiotic resistance markers selected from $Cm^R$, $Sm^R/Sp^R$ and $Tc^R$. A DNA fragment containing the cos site and a replicon can be prepared by releasing the fragment from another cosmid such as, for example, MUA-3, MUA-5, MUA-10, pDPT5Sp, pDPT5Cm, pDPT6, pDPT8 and pDPT9. MUA-3, -5 and -10, are described by Meyerowitz et al, Gene 11:271–282 (1980). Both can be constructed from pBR322 and lambda DNA. MUA-3 and pBR322 are on deposit in the American Type Culture Collection, Rockville, Md., U.S.A., under accession numbers 37069 and 37017, respectively.

Insertion of foreign DNA into cosmid DNA to prepare a cosmid cloning vector of the invention, packaging of the vector and transfection of host cells can be carried out by known techniques. Useful techniques are disclosed in the references cited above, in the background section. There is preferably sufficient foreign DNA to form a recombinant molecule in which the cosmid DNA and the foreign DNA total about 38 to 52 kb.

The above-described cosmid cloning vectors of the invention are desirable because their cosmid DNA is small, has many restriction sites suitable for cloning and subcloning, is comprised of largely defined DNA sequences, contains a multicopy replicon, can be amplified, is mobilizable only in the presence of a conjugal plasmid if mobilization functions are provided in trans, is reasonably stable and contains new combinations of antibiotic resistance markers, offering valuable alternative genetic engineering tools. The last-noted fact makes the vectors especially useful tools when used, for example, in transfection or transformation of cells with one or more additional vectors having complementary resistance markers, such as, for example pACYC177, pSC101 and pHSG422. The vectors also provide alternative unique restrictions sites, simplifying cloning of restriction fragments using unique restriction sites not present in other vectors.

$Cm^R$ and $Sm^R/Sp^R$ markers permit more efficient selection than many other antibiotic resistance markers because their products do not interfere with the action of the respective antibiotic on non-transfected or non-producing cells. By contrast, $\beta$-lactamase, the product of the $Ap^R$ gene, for example, is excreted from producing cells and acts on ampicillin in the medium. $Cm^R$ and $Sm^R/Sp^R$ markers have additional advantages. For example, their products are small, singular proteins produced in relatively small amounts. The products of certain other resistance markers, including $Ap^R$, are large, often fragmented into various size pieces, and are produced in relatively large amounts and, therefore, may interfere with analysis of gene products. By way of further example, chloramphenicol and spectinomycin are stable in stock solutions making their use more convenient than use of several other antibiotics, including rifampicin, tetracycline and ampicillin, which tend to be relatively unstable or light sensitive.

Particular advantages offered by vectors of the invention having $Sm^R/Sp^R$ include that the marker can be used to select transfectants among cells which are $Sm^R$ but not $Sp^R$, such as E. coli HB101. Particular advantages offered by vectors of the invention having $Cm^R$ include that the marker is expressed in Streptomyces.

The plasmid cloning vector of the invention is exemplified by pDPT7 which is about 6.1 kb. It is similar to pDPT9, except that, as explained in Example 3, below, it has an additional HindIII site between the HindIII and SacII sites downstream of the $Sm^R/Sp^R$ gene and lacks the cos site and PstI site. With the exception of the PstI site, pDPT7 has the same unique restriction sites as pDPT9.

EXAMPLES

In the following examples, which are illustrative and not limiting, all temperatures are in degress Celsius. Enzymes and other reagents used in the Examples are commercially available. Buffers used in the Examples were prepared substantially in accordance with vendors' recommendations.

EXAMPLE 1. Construction of pDPT5Cm and pDPT5Sp

Figure 1:
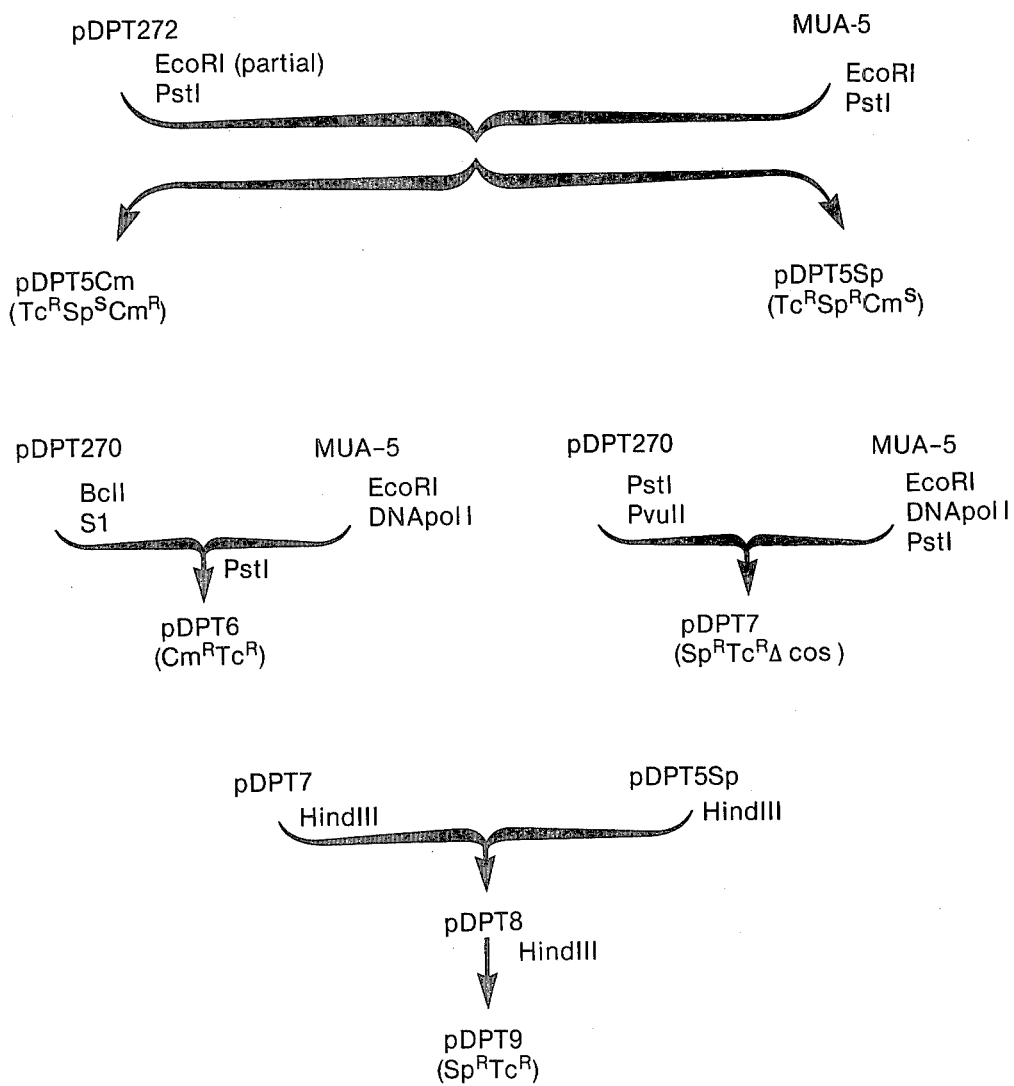
FIG. 1 is a flow sheet illustrating preparation of cosmid cloning vectors of the invention.
Figure 2:
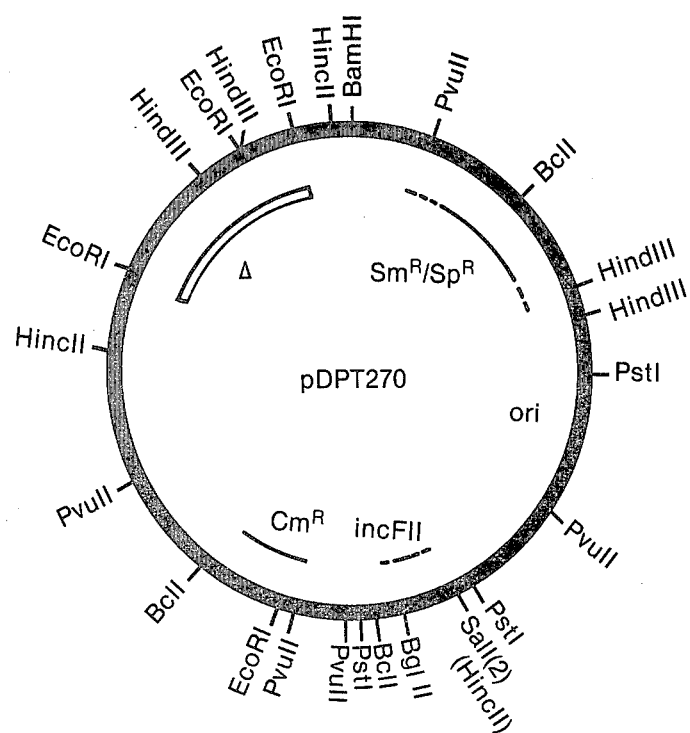
FIG. 2 is a restriction endonuclease cleavage map of pDPT270 showing a deletion for construction of pDPT272.
Figure 3:
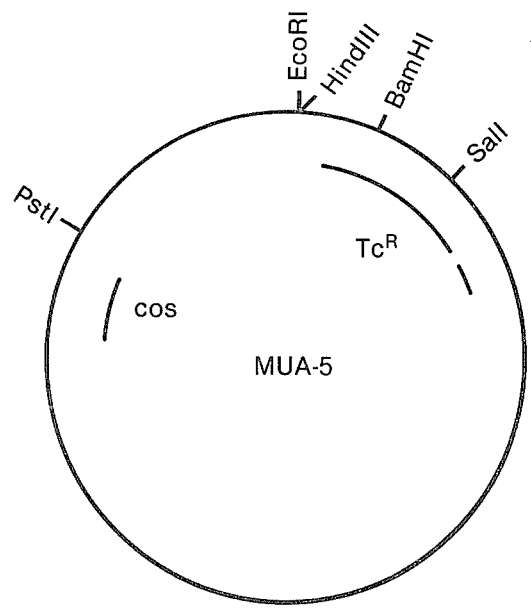
FIG. 3 is a restriction endonuclease cleavage map of MUA-5.

The object of this example was to insert an additional antibiotic resistance marker into MUA-5, illustrated in FIG. 3. MUA-5 was provided by Dr. Gregory M. Guild, University of Pennsylvania, Philadelphia, Pa., U.S.A. The additional resistance markers were derived from pDPT272 which was prepared by in vitro EcoRI deletion of pDPT270, the latter being described by Taylor et al., J. Bacteriol. 137(1):92–104(1979). pDPT270 is illustrated in FIG. 2. The bar in FIG. 2, marked delta, illustrates the EcoRI fragments deleted from pDPT270 to construct pSPT272. The procedure followed is outlined in FIG. 1.

Purified DNA of MUA-5 and pDPT272, was separately digested with PstI and EcoRI. Varying concentrations of EcoRI were used to assure that partial digestions of pDPT272 would produce EcoRI-PstI fragments carrying the $Sm^R/Sp^R$ marker and the $Cm^R$ marker. The fragments from MUA-5 and pDPT272 were mixed without further purification and ligated at a concentration of $10^{-5}$ g/mL at 15° for over 12 hours using 20–40 units of T4 DNA ligase in a volume of 0.1 mL. The ligated fragments were then transformed into cells of E. coli K12 strain MM294 made competent by treatment with $CaCl_2$.

$Tc^R Cm^R$ and $Tc^R Sp^R$ transformants were selected on selective medium. Candidate recombinant plasmids were purified by cesium chloride density gradient centrifugation and analyzed by restriction endonuclease digestion. A $Tc^R Cm^R$ candidate having a restriction pattern corresponding to the map illustrated in FIG. 4 was designated pDPT5Cm. A $Tc^R Sp^R$ candidate having a restriction pattern corresponding to the map illustrated in FIG. 5 was designated pDPT5Sp. Cultures of E. coli K12 strains MM294(pDPT5Cm) and MM294(pDPT5Sp), carrying pDPT5Cm and pDPT5Sp, respectively, have been desposited in accordance with the Budapest Treaty and U.S. Patent and Trademark Office ("USPTO") and European Patent Office ("EPO") regulations in the Agricultural Research Culture Collection, Peoria, Ill., U.S.A., on Sept. 23, 1982 under accession numbers NRRL B-15159 and B-15160, respectively.

EXAMPLE 2. Construction of pDPT6

The object of this example was to prepare a smaller, and hence more useful, $Tc^R Cm^R$ cosmid cloning vector. The procedure followed is outlined in FIG. 1.

MUA-5 DNA was digested with EcoRI and the single strand ends were filled in using DNA polymerase I to produce a linear, blunt-ended fragment. pDPT270 DNA was digested with BclI. A 0.9 Md BclI fragment carrying the $Cm^R$ marker was purified by agarose gel electrophoresis and electroelution. The purified $Cm^R$ fragment, $3 \times 10^{-6}$ g, was treated with 0.1 unit of Sl nuclease for 10 minutes at 37°, extracted with phenol and ether, and precipitated with ethanol.

The $Cm^R$ fragment, $3 \times 10^{-6}$ g, and $2 \times 10^{-6}$ g of the EcoRI-cut and repaired MUA-5 were mixed and digested with 10 units of PstI for 2 hours at 37°. The mixture was incubated at 65° for 10 minutes and then diluted to 0.1 ml and ligated for more than 12 hours at 15° using T4 DNA ligase.

E. coli K12 strain MM294 was treated with $CaCl_2$ and transformed with the ligated fragments. $Tc^R Cm^R$ transformants were selected and found to contain cosmid pDPT6, illustrated in FIG. 6, which consists of a BclI (nuclease-blunted)-PstI fragment of pDPT270 carrying the $Cm^R$ marker and a EcoRI(polymerase-repaired)-PstI fragment of MUA-5 carrying the $Tc^R$ marker, the cos site and the replicon. This cosmid has been deposited within E. coli K12 strain MM294(pDPT6) in accordance with the Budapest Treaty and USPTO and EPO regulations in the Agricultural Research Culture Collection, Peoria, Ill., U.S.A., on Sept. 23, 1982 under accession number NRRL-B-15161.

EXAMPLE 3. Construction of pDPT7 and pDPT8

The object of this example was to prepare a smaller, and hence more useful, $Tc^R Sm^R/Sp^R$ cosmid cloning vector. The procedure followed is outlined in FIG. 1.

MUA-5 DNA was treated as described in Example 2 to produce an EcoRI(polymerase-repaired) blunt-ended linear DNA and then digested with PstI to excise a PstI-EcoRI fragment carrying nonessential DNA. pDPT270 was digested with PstI, PvuII and EcoRI to prepare a 1.5 Md PstI-PvuII fragment carrying the $Sm^R/Sp^R$ marker which fragment was readily purified from the numerous smaller fragments produced by PstI, EcoRI and PvuII by electrophoresis and electroelution.

Treated-MUA-5 DNA, $2 \times 10^{-6}$ g, and $1.6 \times 10^{-6}$ g of the $Sm^R/Sp^R$ fragment were ligated in 0.1 mL with T4 DNA ligase. The ligated fragments were used to transform $CaCl_2$-treated E. coli K12 strain MM294. $Tc^R Sp^R$ transformants were selected and found to contain plasmid pDPT7. This vector has been deposited within E. coli K12 strain MM294 (pDPT7) in accordance with the Budapest Treaty and USPTO and EPO regulations in the Agricultural Research Culture Collection, Peoria, Ill., U.S.A., on Sept. 23, 1982 under accession number NRRL B-15162. Analysis by restriction endonuclease digestion revealed that the cos site and the PstI site bordering the cos site in MUA-5 had been deleted. Other cosmids having the PstI site and cos site intact can be prepared by the above procedure. A HindIII site near the deletion was intact. The EcoRI(-polymerase-repaired)blunt-ended terminus on MUA-5 had joined to the PvuII site on the pDPT270 fragment regenerating an EcoRI site as desired.

To prepare pDPT8, a HindIII fragment of pDPT7, carrying the $Sm^R/Sp^R$ marker, including the regenerated EcoRI site between the $Sm^R/Sp^R$ promoter and the $Tc^R$ promoter, was ligated with the largest HindIII fragment of pDPT5Sp, carrying the cos site, the replicon and the $Tc^R$ marker. By this procedure, a cosmid containing only two, instead of three, HindIII sites and a PstI site was prepared, deleting a small (about 150 base pairs) HindIII fragment. The procedure, illustrated in FIG. 1, was performed by digesting pDPT7 DNA with HindIII, BamHI, and PvuII and pDPT5Sp DNA with HindIII, PvuI and BstEII. The use of the other endonucleases in addition to HindIII was to reduce the probability that the undesired fragments would ligate together to form plasmids that could be selected out of the ligation mixture upon transformation into E. coli. Each digest, $0.5 \times 10^{-6}$ g, was ligated together in 0.1 mL using T4 DNA ligase and the mixture was transformed into E. coli K12 strain MM294. $Tc^R$ $Sp^R$ transformants were selected and screened for cosmids of the appropriate size. The cosmid chosen for further study was designated pDPT8 and mapped with restriction endonucleases. The mapping indicated that the $Sp^R$ segment was in the opposite orientation relative to pDPT5Sp and pDPT7. In pDPT8, the expression of the $Tc^R$ gene is presumed to be driven by transcription initiated at the $Sp^R$ gene promoter reading through the $Sp^R$ gene into the $Tc^R$ operon. Thus, if a fragment were inserted into the $Sp^R$ gene, inactivating $Sp^R$, the expression of $Tc^R$ might also be prevented.

pDPT8 has been deposited within E. coli K12 strain MM294(pDPT8) in accordance with the Budapest Treaty and USPTO and EPO regulations in the Agricultural Research Culture Collection, Peoria, Ill., U.S.A., on Sept. 23, 1982 under accession number NRRL B-15163.

EXAMPLE 4. Construction of pDPT9

The orientation of the $Sp^R$ segment in pDPT8 was reversed by scrambling with HindIII. pDPT8 DNA, $2 \times 10^{-6}$ g, was digested with HindIII, ligated with T4 DNA ligase and used to transform competent cells of E. coli K12 strain MM294. $Tc^R$ $Sp^R$ transformants were selected. Cosmids with the desired orientation were obtained by digesting DNA with SphI and a candidate with the appropriate size fragments was chosen and designated pDPT9, a map of which is illustrated in FIG. 7. This cosmid has been deposited within E. coli K12 strain MM294(pDPT9) in accordance with the Budapest Treaty and USPTO and EPO regulations in the Agricultural Research Culture Collection, Peoria, Ill., U.S.A., on Sept. 23, 1982 under accession number NRRL-B-15164.

EXAMPLE 5. Cosmid Cloning of Foreign DNA

A. The cosmid cloning vector, pDPT5Cm, was used to clone foreign DNA, namely, BamHI fragments, including one carrying a gene for kanamycin resistance ($Km^R$), of a plasmid designated A'::Tn5. A'::Tn5 is a plasmid with a molecular weight of $6.5 \times 10^7$ Md, which has six BamHI sites. A'::Tn5 DNA was partially digested with BamHI and pDPT5Cm was completely digested with BamHI. Digested pDPT5Cm, $7.2 \times 10^{-6}$ g, and $22 \times 10^{-6}$ g of digested A'::Tn5 DNA were ligated, without fractionation, in 0.02 mL using T4 DNA ligase. Ligated DNA, $1.5 \times 10^{-6}$ g, was packaged according to the procedure of Hohn, Methods in Enzymology 68, 299-309. Samples of packaged DNA were used to transfect E. coli K12 strain MM294 and $Cm^R$ colonies were selected. The efficiency of recovery of $Cm^R$ transfectants was estimated at $2.3 \times 10^8$/g. Thirty-six percent of the $Cm^R$ transfectants were $Tc^S$, indicating that a BamHI fragment had been inserted into the cosmid vector, inactivating $Tc^R$. This frequency of $Tc^S$ transfectants is not a true indication of the frequency of recombinant formation but rather underestimates it. When the frequency of $Km^R$ transfectants was estimated, almost 30% were $Tc^R$. If similar results were obtained for all fragments, then the frequency of recombinant formation should approach 50%. The $Tc^R$ recombinants probably arose by joining of two vectors in a head-to-tail arrangement. The low efficiency given in this example is probably due to the unfavorable size distribution of the BamHI fragments generated by digestion of the A'::Tn5 DNA and because no efforts were made to obtain BamHI fragments of the size needed for efficient packaging. Twenty-six clones including $Tc^S$ and four $Km^R$ candidates were examined by further characterization of plasmid DNA and demonstrated to contain the desired DNA inserts.

B. The cosmid cloning vector, pDPT5Sp, was used to clone foreign DNA, namely, EcoRI fragments, including one carrying a gene for $Km^R$, of the plasmid A'::Tn5, which contains nine EcoRI sites. pDPT5Sp DNA was digested completely with EcoRI and A'::Tn5 DNA was partially digested with EcoRI but not size-fractionated. The DNAs were ligated and packaged as described in A, above. $Sp^R$ transfectants were obtained at an efficiency estimated at $2.8 \times 10^{11}$/g. The EcoRI site on pDPT5Sp is not within either of the antibiotic resistance structural genes so insertional inactivation of a marker cannot be followed. The frequency of $Km^R$ transfectants was determined to be 4% and by examining the DNA of 36 $Sp^R$ transfectants, 36% were found to possess inserts of significant size. As in Example 4, the efficiency of packaging and the frequency of inserts would have been improved had efforts had been made to obtain a more random distribution of fragment sizes and to fractionate the DNA to generate DNA most suitable for packaging.

These results demonstrate that the cosmids of the invention can be utilized as cosmid cloning vectors. The preparation of foreign DNA need not be limited to the DNA or the procedures illustrated. For example, a structural gene for other protein products can be used as the foreign DNA; partial digestion of foreign DNA with other endonucleases, such as endonucleases recognizing a tetrameric sequence, or by shearing DNA to a desired size and adding oligonucleotide linkers can also be employed.

All of the above referenced deposits will be available to the public upon issuance of a U.S. Patent on this or a related application or upon publication of a European Patent Application on this or a related application, whichever is earlier.

I claim:
1. The cosmid cloning vector, pDPT6.
2. The cosmid cloning vector, pDPT8.
3. The cosmid cloning vector, pDPT9.
4. The cosmid cloning vector, pDPT5Cm.
5. The cosmid cloning vector, pDPT5Sp.
6. The plasmid cloning vector, pDPT7.

* * * * *